(12) United States Patent
Vozka et al.

(10) Patent No.: US 9,018,592 B2
(45) Date of Patent: Apr. 28, 2015

(54) DEVICE FOR UV-SPECTROMETRIC ANALYSIS OF GASEOUS COMPOUNDS

(75) Inventors: Stanislav Vozka, Prague 9 (CZ); Miroslav Podolak, Prague 6 (CZ)

(73) Assignee: Labio A.S., Prague (CZ)

( * ) Notice: Subject to any disclaimer, the term of this patent is extended or adjusted under 35 U.S.C. 154(b) by 239 days.

(21) Appl. No.: 13/699,283

(22) PCT Filed: Mar. 16, 2011

(86) PCT No.: PCT/EP2011/053989
§ 371 (c)(1),
(2), (4) Date: Jun. 4, 2013

(87) PCT Pub. No.: WO2011/147602
PCT Pub. Date: Dec. 1, 2011

(65) Prior Publication Data
US 2014/0145087 A1    May 29, 2014

(30) Foreign Application Priority Data
May 24, 2010   (CZ) ................. PV 2010-398

(51) Int. Cl.
*G01J 1/42*   (2006.01)
*G01N 21/33*  (2006.01)
*G01J 3/02*   (2006.01)
*G01J 3/42*   (2006.01)
*G01N 21/09*  (2006.01)
*G01N 21/15*  (2006.01)

(52) U.S. Cl.
CPC ............... *G01N 21/33* (2013.01); *G01J 3/0205* (2013.01); *G01J 3/0291* (2013.01); *G01J 3/42* (2013.01); *G01N 21/09* (2013.01); *G01N 21/15* (2013.01);

(Continued)

(58) Field of Classification Search
CPC ............... G01J 4/18; G01J 3/28; G01N 21/33
USPC ........................................ 250/373
See application file for complete search history.

(56) References Cited

U.S. PATENT DOCUMENTS 4,188,534 A * 2/1980 Watanabe et al. ............. 250/345
4,255,052 A * 3/1981 Anderson ..................... 356/316

(Continued)

FOREIGN PATENT DOCUMENTS

DE    10318786 A1   11/2004
EP    0591758 A1    4/1994

OTHER PUBLICATIONS

International Search Report and Written Opinion received for PCT Patent Application No. PCT/EP2010/53989, mailed on Jun. 9, 2011, 10 pages.

*Primary Examiner* — Kiho Kim
(74) *Attorney, Agent, or Firm* — Morrison & Foerster LLP

(57) ABSTRACT

A device for UV-spectrometric analysis of gaseous compounds includes a measurement channel, a window member transparent for ultraviolet radiation, a radiation source capable of generating ultraviolet radiation, and a spectrographic member for measuring of ultraviolet radiation emitted by the radiation source. The device is arranged such that ultraviolet radiation entering the measurement channel can propagate through the measurement channel, interact with the accommodated gas and be measured by the spectrographic member. An end of the measurement channel is open towards the window member and a channel for guiding a protection gas is arranged in connection to the window member such that protection gas fed through the protection gas channel is allowed to flow over and cover the side of the window member facing the measurement channel and to flow further into the measurement channel.

17 Claims, 1 Drawing Sheet

(52) U.S. Cl.
    CPC .... *G01N 2021/151* (2013.01); *G01N 2021/335* (2013.01)

(56) References Cited

U.S. PATENT DOCUMENTS

| | | | |
|---|---|---|---|
| 4,668,091 A | 5/1987 | Lagesson et al. | |
| 4,927,265 A * | 5/1990 | Brownlee | 356/73 |
| 5,225,681 A | 7/1993 | Falk et al. | |
| 5,804,827 A * | 9/1998 | Akagawa et al. | 250/370.06 |
| 6,305,213 B1 | 10/2001 | Lagesson et al. | |
| 6,423,249 B1 * | 7/2002 | Leveille | 252/588 |
| 7,525,664 B2 * | 4/2009 | Dani et al. | 356/437 |
| 2007/0009385 A1 * | 1/2007 | Watanabe | 422/68.1 |
| 2007/0273882 A1 | 11/2007 | Smith | |
| 2008/0011049 A1 * | 1/2008 | Dani et al. | 73/23.2 |

* cited by examiner

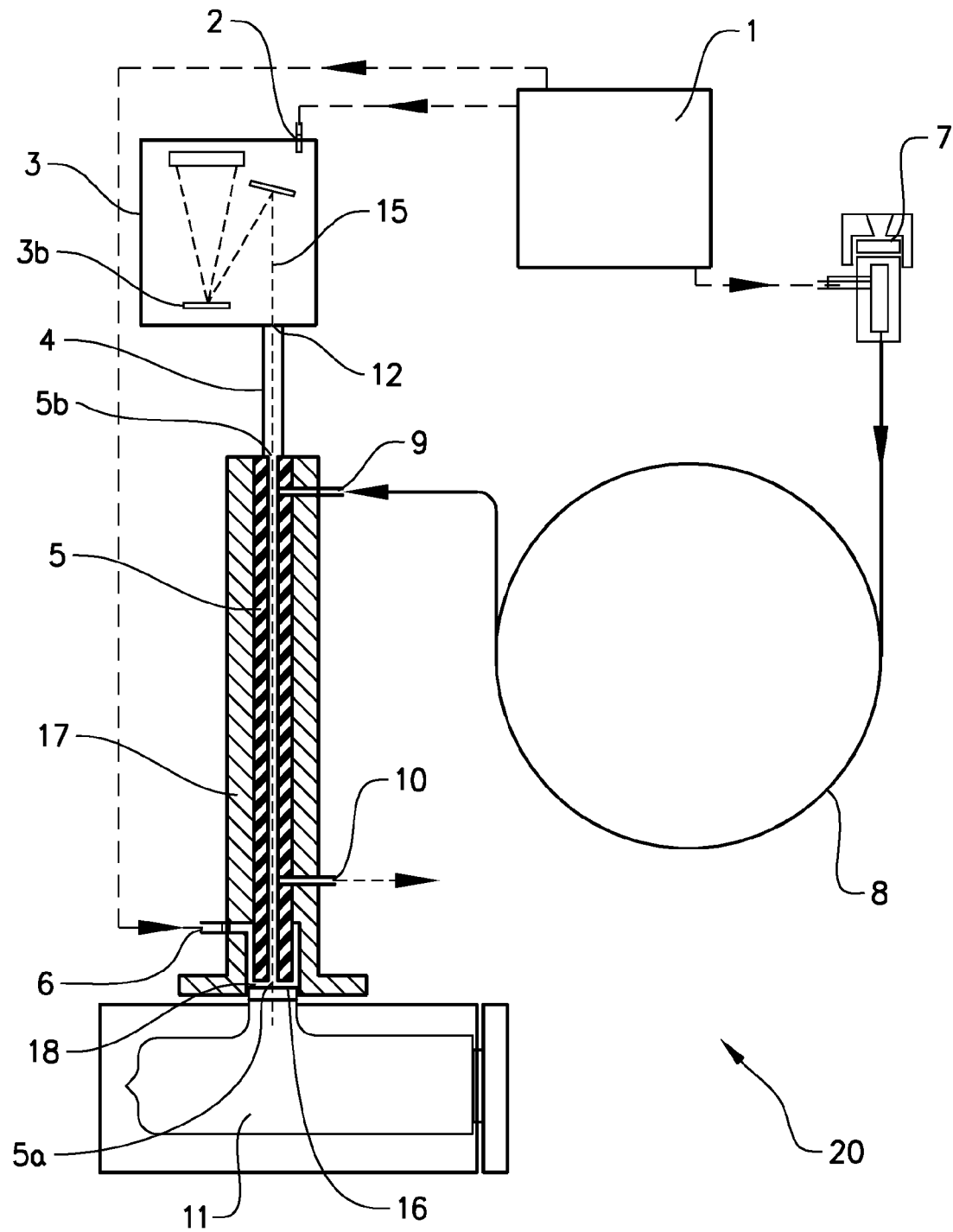

DEVICE FOR UV-SPECTROMETRIC ANALYSIS OF GASEOUS COMPOUNDS

CROSS REFERENCE TO RELATED APPLICATIONS

This is a U.S. National Phase patent application of PCT/EP2011/053989, filed Mar. 16, 2011, which claims priority to the Czech Patent Application No. PV 2010-398, filed May 24, 2010, each of which is hereby incorporated by reference in the present disclosure in its entirety.

TECHNICAL FIELD

This invention relates to a device for UV-spectrometric analysis of gaseous compounds according to the preamble of claim 1. In particular, the invention relates to measurements of UV radiation with wavelengths in the far UV region.

BACKGROUND OF THE INVENTION

Spectrophotometric measurement of gas and vapour absorption is well known in various applications. An example is analytical chemistry where ultraviolet (UV) spectrometers are combined with gas chromatography (GC) for determining gaseous compounds. Examples of equipment for such use are disclosed in U.S. Pat. No. 4,668,091 and U.S. Pat. No. 6,305,213. Various UV spectrometers or spectrographs as well as gas chromatographs are commercially available.

Ultraviolet radiation has a wavelength shorter than that of visible light but longer than X-rays, in the range 10-400 nm, and its spectrum can be subdivided in a number of ways, for instance, near UV 400-300 nm, middle UV 300-200 nm, far UV 200-122 and vacuum UV 200-100 nm. Ordinary glass is opaque to shorter wavelengths. Windows made of quartz glass are normally used when analyzing wavelengths shorter than around 350 nm. Wavelengths shorter than around 190 nm, i.e. radiation in the far UV or vacuum region, are normally absorbed too strongly also in quartz. In this wavelength region it is possible to use windows and other optical elements made of alkaline earth metal fluorides, such as $MgF_2$. However, such materials are not as resistant to chemicals as quartz and there are a number of applications where these materials are not suitable. This is in particular a problem at elevated temperatures.

UV wavelengths in the far UV or vacuum region is of great interest in chemical analysis since most chemical compounds absorb light in that region. Many compounds that cannot be detected at longer wavelengths may be analyzed using radiation in the far UV region. However, also air, or rather oxygen ($O_2$) and water vapour, absorbs light strongly in this region (in the range below around 190 nm) which means that the analytic equipment must be specially adapted to avoid interference from air. For this purpose there are, for instance, UV spectrographs commercially available that are adapted to be evacuated or to be filled with an inert gas, such as nitrogen ($N_2$) (which absorbs UV only at very short wavelengths).

Equipment for analyzing gases and/or vapours with UV spectroscopy typically includes an elongated heated channel (cell) that accommodates a sample gas during measurement, a UV-source (e.g. a deuterium lamp) positioned at one end the channel and a UV detector (a UV spectrograph) located at the opposite end of the channel. Gas tight and UV-transparent windows, typically made of quartz, are provided at each end of the channel. The channel may be provided with inlets and outlets for leading sample gas, e.g. from a GC, and carrier gas to and from the channel in a continuous manner. UV light emitted by the UV-source passes through the window of the UV-source, through the entrance window of the channel and into and through the channel where part of the light is absorbed in the sample gas. Remaining radiation passes the exit window of the channel and enters the UV spectrograph through a window or slit. The UV spectrograph measures the intensity at different wavelengths of the UV radiation that has passed through the channel and the absorption spectra obtained is used to identify and quantify the compounds present in the sample gas.

To adapt such equipment to measurements of radiation in the far UV region a UV transparent (e.g. evacuated) UV detector can be used and the quartz windows can be replaced by windows made of an alkaline earth metal fluoride. However, such an adaptation works well only in situations where the sample gas does not contain compounds that may decompose the sensitive material of the channel windows. Such degradation of the channel windows is difficult to prevent in many cases, in particular at elevated temperatures, such as when the sample gas is supplied from a heated column of a gas chromatograph, Accordingly, there is a need for improvements in the field of equipment for use in far UV spectroscopy analysis of a gas.

SUMMARY OF THE INVENTION

An object of this invention is to provide a device for UV-spectrometric analysis of gaseous compounds that exhibit improved capabilities of performing analysis of radiation in the far UV region compared to conventional devices. This object is achieved by the device defined by the technical features contained in independent claim 1. The dependent claims contain advantageous embodiments, further developments and variants of the invention.

The invention concerns a device for UV-spectrometric analysis of gaseous compounds, said device comprising: a measurement channel intended to accommodate a flow of sample gas to be analyzed, a window member transparent for ultraviolet radiation arranged at a first end of the measurement channel, a radiation source capable of generating ultraviolet radiation arranged to emit radiation through the window member and into the measurement channel, and a spectrographic member for measuring of ultraviolet radiation emitted by the radiation source arranged at a second, opposite, end of the measurement channel, wherein the device is arranged such that ultraviolet radiation entering the measurement channel at the first end can propagate through the measurement channel, interact with the accommodated gas and be measured by the spectrographic member at the second end of the measurement channel.

The invention is characterized in that the first end of the measurement channel is open towards the window member and in that a channel for guiding a protection gas is arranged in connection to the window member such that protection gas fed through the protection gas channel is allowed to flow over and cover the side of the window member facing the measurement channel and to flow further into the measurement channel.

The inventive design has the advantageous effect that it makes it possible to prevent sample gas (and its content of potentially corrosive compounds) in the measurement channel to come into contact with the window member by feeding protection (inert) gas through the protection gas channel. Since the protection gas passes the window member and then flows into the measurement channel via its open end it stops the sample gas in the channel and protects the window member. The invention thereby allows the use of a channel entrance window made of an alkaline earth metal fluoride, such as $MgF_2$, which is likely to be sensitive to compounds in the sample gas but at the same time is transparent to shorter UV wavelengths.

Nitrogen ($N_2$) is a suitable protection gas in that it protects the window well and is transparent to UV radiation at wavelengths above around 150 nm. The flow of $N_2$ or other suitable protection gas is useful also for use as carrier gas and for removing oxygen water vapour from the measurement channel.

The invention thus solves the problem of arranging the UV entrance window such that UV radiation in the far UV region can enter the measurement channel without risking degradation of the sensitive window material. To be able to perform a proper UV analysis of the sample gas also the UV exit window at the second end of the measurement channel must be properly arranged so that UV radiation in the far UV region can exit the measurement channel and enter the spectrographic member. This can be done by a similar arrangement, i.e. by arranging a second window at the second end of the measurement channel and by arranging a corresponding protection gas channel in connection to the second window member. Alternatively, the UV exit window can be arranged as a "gas window" as described further below.

In an embodiment of the invention a void is arranged adjacent the window member at the side of the window member facing the measurement channel, wherein the void is in communication with the open end of the measurement channel and wherein the void is provided with a void inlet such that when a protection gas is fed to said void inlet, the protection gas is allowed to fill the void and flow further into the measurement channel.

In an embodiment of the invention the measurement channel is provided with at least one inlet for feeding sample gas into the measurement channel and at least one outlet for leading sample gas and protection gas out from the measurement channel.

In an embodiment of the invention the spectrographic member is provided with an opening through which ultraviolet radiation passes into the spectrographic member during operation of the device, wherein the second end of the measurement channel is open towards the spectrographic member such that an inside of the spectrographic member and the measurement channel are in communication via said opening, wherein the spectrographic member is arranged to be filled with a protection gas, and wherein the device is arranged such that protection gas fed to the spectrographic member is allowed to flow through said opening and into the measurement channel.

By feeding protection gas through the spectrographic member via the opening (typically a slit) and further into the measurement channel, the protection gas forms a "gas window" that dispenses with the need for arranging a normal, solid exit window at this side of the measurement channel. Using a proper protection gas, such as $N_2$, the gas window formed can be made to be transparent to UV radiation of sufficiently short wavelength without the use of e.g. $MgF_2$ which is not only a sensitive material but also costly.

The protection gas entering the measurement channel via the opening in the spectrographic member can work as a carrier gas for the sample gas in the measurement channel before it is lead out via the at least one outlets. By properly adjusting the gas pressures the sample gas will not flow towards, or at least not through, the opening of the spectrographic member.

The protection gas supplied to the spectrographic member thus has at least two functions: to remove Interfering gases, such as $O_2$ and $H_2O$, from the spectrographic member (and at least a part of the measurement channel), and to form a "window" that allows ultraviolet radiation to pass but that prevents sample gas to escape. Depending on the design of e.g. the inlets and outlets of the measurement channel the protection gas supplied to the spectrographic member can also function as carrier gas.

Together with the gas arrangement at the window member at the first end of the device, this allows for UV spectrometric analysis of UV radiation with wavelengths shorter than 190 nm down to around 150 nm depending on the protection gas used.

Using protection gas for forming the window at the spectrographic member is less complicated and less costly compared to arranging a gas protected $MgF_2$-window also at this side of the measurement channel.

In an embodiment of the invention the device comprises seal members arranged such as to prevent air that surrounds the device from entering the measurement channel.

In an embodiment of the invention the device comprises a gas chromatography column for connection to the sample gas inlet.

In an embodiment of the invention the device comprises a gas flow regulator arranged to regulate the flow of protection gas fed to the protection gas channel.

In an embodiment of the invention the gas flow regulator is arranged to regulate the flow of sample gas.

In an embodiment of the invention the gas flow regulator is arranged to regulate the flow of protection gas fed to the spectrographic member.

In an embodiment of the invention the measurement channel has an elongated shape, wherein the window member and the spectrographic member are positioned at opposite ends of the measurement channel.

In an embodiment of the invention the measurement channel is a silica tube.

In an embodiment of the invention the measurement channel is arranged in a casing adapted to be heated.

In an embodiment of the invention the radiation source is a deuterium lamp. Preferably, the window member forms an integrated part of the deuterium lamp.

In an embodiment of the invention the window member is made of an alkaline earth metal fluoride. Preferably, the window member is made of $MgF_2$.

In an embodiment of the invention the spectrographic member comprises reflectors and registration element adapted to short wavelength ultraviolet radiation.

BRIEF DESCRIPTION OF DRAWINGS

In the description of the invention given below reference is made to the following FIGURE, in which:

FIG. 1 shows, in a schematic view, an embodiment of the invention.

DESCRIPTION OF EXAMPLE EMBODIMENTS OF THE INVENTION

FIG. 1 shows an embodiment of a device 20 for UV-spectrometric analysis of gaseous compounds. The device 20 comprises a gas flow regulator 1, a spectrographic member 3, a connecting tube 4, a measurement channel 5, a sample injector 7, a gas chromatography packed column 8 and a UV-source 11 in the form of a deuterium lamp.

The spectrographic member 3 is in this example a grating spectrograph containing exclusively reflective optical elements 3b with a long registration element capable of registering UV light of very short wavelength. The spectrographic member 3 is provided with an inlet 2 for supplying protection gas into the member 3 and an opening 12 in the form a slit for admitting UV radiation (dashed line 15) that has passed through the measurement channel 5 to enter the spectrographic member 3. The connecting tube 4 is arranged in a sealed (gas tight) manner around the slit 12 and around a second open end 5b of the measurement channel 5 facing the spectrographic member 3. The tube 4 is arranged as an extension of the measurement channel 5. The spectrographic member 3 is gas tight which means that when the spectrographic member 3 has been filled with protection gas through the inlet 2 the gas will flow out through the slit 12 through the tube 4 and further into the measurement channel 5 via its open end 5b.

The deuterium lamp 11 is positioned at an opposite end of the measurement channel 5 in relation to the spectrographic member 3. A window member 16 that forms an integrated part of the deuterium lamp 11 is facing a first open end 5a of the measurement channel 5. The window member 16 is made of $MgF_2$ and it is arranged in a sealed (gas tight) manner in association with the first end 5a of the measurement channel 5.

The sample injector 7 is arranged to inject sample gas to the gas chromatography column 8.

The measurement channel 5 is a tube made of pure silica and it is arranged in a housing 17 adapted to be heated such as to keep the measurement channel 5 at a controlled, elevated temperature during operation of the device 20. An inlet 9 for introducing the sample gas into the measurement channel 5 is arranged in the measurement channel 5 in a position relatively close to the second end 5b of the channel 5 facing the spectrographic member 3. An outlet 10 for leading sample gas and protection gas out from the measurement channel 5 is positioned relatively close to the first end 5a of the channel 5 facing the UV source 11. An inlet 6 for protection/inert gas is arranged in association with the first end 5a of the channel 5 facing the UV source 11 so that gas fed to the this inlet 6 enters a void 18 between the window member 16 and the channel 5 so that this gas flushes over, covers and protects the side of the window member 16 facing the channel 5 before the gas continues to flow into the channel 5 through the open end 5a thereof.

The gas flow regulator 1 is arranged such as to feed a carrier gas through the column 8 and to feed protection gas (which in this case is the same gas as the carrier gas: $N_2$) to the inlet 2 of the spectrographic member 3 and to the inlet 6 at the window member 16.

During operation of the device 20, the gas flows are adjusted such that gas supplied to the spectrographic member 3 via the inlet 2 fills the spectrographic member 3 and flows further into the measurement channel 5 via the slit 12, the tube 4 and the open end 5b of the channel 5. The sample gas entering the channel 5 via the inlet 9 mixes with the flow (of nitrogen) from the spectrographic member 3 and flows through the channel 5 towards the UV source 11.

Simultaneously, protection or inert gas is fed to the inlet 6 at the window member 16. This gas flow fills the void 18 and contacts and covers the window member 16 and flows further into the channel 5 towards the spectrographic member 3. At the position of the outlet 10 the two oppositely directed gas flows in the channel 5 meet and mix, and flow out from the measurement channel 5 via the outlet 10. Preferably, protection/inert gas is allowed to enter the open ends 5a, 5b of the channel 5 before sample gas is introduced through the inlet 9.

Measurement of the sample gas can be carried out while it flows along the measurement channel 5. Because a gas chromatography column 8 that separates compounds is arranged upstream of the measurement channel 5, it is likely that only one or at least only a few sample gas compounds will be present in the measurement channel 5 at the same time. The result of the measurement carried out by the spectrographic member 3 is typically a spectrum showing the absorption of UV-radiation as a function of both wavelength and time.

The device 20 also comprises a control unit (not shown) for controlling the various parts of the device 20, such as the gas flow regulator 1 (for controlling the gas flows), the UV-source 11, the spectrographic member 3, the heating of the casing 17 and the column 8, and the sample injector 7.

EXAMPLE 1

A device according to the invention was assembled containing a deuterium lamp with an exit window made of $MgF_2$ (Hamamatsu, Japan), a cell/measurement channel made from a silica tube (I.D. 1 mm, 200 mm long), inserted and fused into a heated Al bar of square cross-section provided with input fitting for gases and silicon seals both at the lamp and the spectrograph (Photon Control, Canada) with a grating 1,200 grooves/mm, optimised for 300 nm, and an optical element CCD Toshiba TCD1304 CCD with the silica glass cover removed (such as to create an opening). All components were mounted on an optical bench made of an aluminium angle bar (100 mm×100 mm×10 mm). A stream of inert gas (nitrogen, purity 5.0) entered an opening made in the central part of the cell from a loop injector, used to add the compounds whose spectra were to be measured into the inert gas stream. Additional inert gas entered the inlet close to the lamp window and also to the spectrograph which was properly sealed to ensure that the gas could exit only through the slit by which light from the flow cell enters. The gas flows were controlled in a manner ensuring that the analysed compounds did not contact or even got close to the lamp window. The instrument was used to measure spectra of aromatic hydrocarbons and ketones.

EXAMPLE 2

The spectrometer described in Example 1 was connected to a gas chromatograph (Labio, Czech Republic) with a chromatographic column of 2 mm diameter, 4 m long, packed with Supelcoport OV1 sorbent (Sigma Aldrich). Mixtures of organic compounds dissolved in an aliphatic solvent were injected and spectra were measured and recorded as a function of time.

The invention is not limited by the embodiments described above but can be modified in various ways within the scope of the claims.

For instance, the gas inlets and outlets to and from the measurement channel 5 can be arranged in different ways. Generally it is advantageous if the sample gas is allowed to flow along most of the length of the channel 5 to let the UV light (dashed line 15) pass as much sample gas as possible before entering the spectrographic member 3. This increases normally the sensitivity of the analysis. Sample gas may enter the measurement channel 5 at a position close to the first end 5a of the channel facing the UV source 11 (with an outlet arranged close to the second end 5b of the channel 5 facing the spectrographic member 3) or sample gas may be fed to a mid section of the measurement channel 5 (preferably with one outlet arranged at each end of the channel 5 so that the flow of sample gas can divide and flow in different directions towards each end of the channel 5). Of course, the gas flows must be regulated so that sample gas is prevented from coming into contact with the window member 16 and from entering the spectrographic member 3.

Moreover, the UV source 11 does not necessarily have to be a deuterium lamp.

The invention claimed is:

1. Device for UV-spectrometric analysis of gaseous compounds, said device comprising:
    a measurement channel configured to accommodate a flow of sample gas to be analyzed,
    a window member transparent for ultraviolet radiation arranged at the first end of the measurement channel,
    a radiation source capable of generating ultraviolet radiation arranged to emit radiation through the window member and into the measurement channel,
    a spectrographic member for measuring of ultraviolet radiation emitted by the radiation source arranged at a second, opposite, end of the measurement channel,
    wherein the device is arranged such that ultraviolet radiation entering the measurement channel at the first end can propagate through the measurement channel, interact with the accommodated gas and be measured by the spectrographic member at the second end of the measurement channel,
    wherein the first end of the measurement channel is open towards the window member and a channel for guiding a protection gas directly toward the window member is arranged such that protection gas fed through the protection gas channel is allowed to flow over and cover the side of the window member facing the measurement channel and to flow further into the measurement channel.

2. Device according to claim 1, wherein a void is arranged adjacent the window member at the side of the window member facing the measurement channel, wherein the void is in communication with the open end of the measurement channel and wherein the void is provided with a void inlet such that when a protection gas is fed to said void inlet, the protection gas is allowed to fill the void and flow further into the measurement channel.

3. Device according to claim 1, wherein the measurement channel is provided with at least one inlet for feeding sample gas into the measurement channel and at least one outlet for leading sample gas and protection gas out from the measurement channel.

4. Device according to claim 1, wherein the spectrographic member is provided with an opening through which ultraviolet radiation passes into the spectrographic member during operation of the device, wherein the second end of the measurement channel is open towards the spectrographic member such that an inside of the spectrographic member and the measurement channel are in communication via said opening, wherein the spectrographic member is arranged to be filled with a protection gas, and wherein the device is arranged such that protection gas fed to the spectrographic member is allowed to flow through said opening and into the measurement channel.

5. Device according to claim 1, further comprising seal members arranged such as to prevent air that surrounds the device from entering the measurement channel.

6. Device according to claim 1, further comprising a gas chromatography column for connection to the sample gas inlet.

7. Device according to claim 1, further comprising a gas flow regulator arranged to regulate the flow of protection gas fed to the protection gas channel.

8. Device according to claim 1, wherein the gas flow regulator is arranged to regulate the flow of sample gas.

9. Device according to claim 1, wherein the gas flow regulator is arranged to regulate the flow of protection gas fed to the spectrographic member.

10. Device according to claim 1, wherein the measurement channel has an elongated shape, wherein the window member and the spectrographic member are positioned at opposite ends of the measurement channel.

11. Device according to claim 10, wherein the measurement channel is a silica tube.

12. Device according to claim 1, wherein the measurement channel is arranged in a casing adapted to be heated.

13. Device according to claim 1, wherein the radiation source is a deuterium lamp.

14. Device according to claim 13, wherein the window member forms an integrated part of the deuterium lamp.

15. Device according to claim 1, wherein the window member is made of an alkaline earth metal fluoride.

16. Device according to claim 15, wherein the window member is made of $MgF_2$.

17. Device according to claim 1, wherein the spectrographic member comprises reflectors and registration element adapted to short wavelength ultraviolet radiation.

* * * * *